United States Patent [19]

Oppong et al.

[11] Patent Number: 5,776,960
[45] Date of Patent: Jul. 7, 1998

[54] SYNERGISTIC ANTIMICROBIAL COMPOSITIONS CONTAINING AN IONENE POLYMER AND A PYRITHIONE SALT AND METHODS OF USING THE SAME

[75] Inventors: David Oppong; Russel E. Fues, both of Memphis, Tenn.; Graciela H. Vunk, Olive Branch, Miss.

[73] Assignee: Buckman Laboratories International, Inc., Memphis, Tenn.

[21] Appl. No.: 731,578

[22] Filed: Oct. 16, 1996

[51] Int. Cl.⁶ .......................... A01N 43/40; A01N 52/02
[52] U.S. Cl. .................. 514/345; 424/78.09; 424/78.37; 514/188
[58] Field of Search ...................... 514/188, 345; 424/78.09, 78.37

[56] References Cited

U.S. PATENT DOCUMENTS

| | | | |
|---|---|---|---|
| Re. 28,808 | 5/1976 | Panzer et al. | 260/2 BP |
| 2,809,971 | 10/1957 | Bernstein et al. | 260/270 |
| 3,159,640 | 12/1964 | McClure et al. | 260/294.8 |
| 3,231,509 | 1/1966 | Shema | 252/177 |
| 3,236,733 | 2/1966 | Karsten et al. | 167/87 |
| 3,738,945 | 6/1973 | Panzer | 260/2 BP |
| 3,778,476 | 12/1973 | Rembaum et al. | 260/567.6 P |
| 3,874,870 | 4/1975 | Green et al. | 71/67 |
| 3,894,946 | 7/1975 | Panzer et al. | 210/54 |
| 3,894,947 | 7/1975 | Panzer et al. | 210/54 |
| 3,898,336 | 8/1975 | Rembaum et al. | 424/25 |
| 3,930,877 | 1/1976 | Aitken | 106/287 |
| 3,931,319 | 1/1976 | Green et al. | 260/567.6 P |
| 4,025,627 | 5/1977 | Green et al. | 424/248.4 |
| 4,027,020 | 5/1977 | Green et al. | 424/248.56 |
| 4,054,542 | 10/1977 | Buckman et al. | 260/2 BP |
| 4,089,977 | 5/1978 | Green et al. | 424/329 |
| 4,104,161 | 8/1978 | Wein | 210/54 |
| 4,111,679 | 9/1978 | Shair et al. | 71/67 |
| 4,147,627 | 4/1979 | Goodman | 210/58 |
| 4,164,521 | 8/1979 | Goodman | 525/187 |
| 4,166,041 | 8/1979 | Goodman | 252/180 |
| 4,506,081 | 3/1985 | Fenyes et al. | 548/523 |
| 4,565,856 | 1/1986 | Trotz et al. | 526/265 |
| 4,581,058 | 4/1986 | Fenyes et al. | 71/67 |
| 4,596,864 | 6/1986 | Trotz et al. | 526/265 |
| 4,606,773 | 8/1986 | Novak | 106/213 |
| 4,632,881 | 12/1986 | Trotz et al. | 428/541 |
| 4,769,155 | 9/1988 | Dwyer | 210/728 |
| 4,778,813 | 10/1988 | Fenyes et al. | 514/357 |
| 4,970,211 | 11/1990 | Fenyes et al. | 514/252 |
| 5,051,124 | 9/1991 | Pera | 71/67 |
| 5,093,078 | 3/1992 | Hollis et al. | 422/16 |
| 5,614,538 | 3/1997 | Nelson | 514/188 |

FOREIGN PATENT DOCUMENTS

| | | |
|---|---|---|
| 0 286 453 | 10/1988 | European Pat. Off. . |
| 0 368 593 | 5/1990 | European Pat. Off. . |
| 0 420 631 | 4/1991 | European Pat. Off. . |
| 5415939 | 2/1979 | Japan ........................ 514/188 |
| 56-61308 | 5/1981 | Japan . |
| 1 390 004 | 4/1975 | United Kingdom . |
| 1390004 | 4/1975 | United Kingdom . |
| WO 90/06125 | 6/1990 | WIPO . |
| 96 17724 | 6/1996 | WIPO . |

OTHER PUBLICATIONS

Kull et al., "Mixtures of Quaternary Ammonium Compounds and Long–Chain Fatty Acids as Antifungal Agents," *Applied Microbiology*, vol. 9, pp. 538–541, 1961.

Abstract No. 193370, Michael J. Zabik, et al., Chemical Abstract, vol. 109, No. 22, "Unique Use of a Cationic Microbicide for Extending the Life of a Synthetic Metal Working Fluid in a Manufacturing Environment—a Case History", Nov. 28, 1988.

*Primary Examiner*—Allen J. Robinson
*Attorney, Agent, or Firm*—Armstong, Westerman, Hattori, McLeland & Naughton

[57] ABSTRACT

Compositions comprising an ionene polymer and a pyrithione salt are disclosed which are synergistically effective compared to the respective components alone in controlling the growth of microorganisms in or on a material or medium. Methods to control the growth of microorganisms and prevent spoilage caused by microorganisms with the use of the compositions of the present invention are also disclosed.

41 Claims, No Drawings

SYNERGISTIC ANTIMICROBIAL COMPOSITIONS CONTAINING AN IONENE POLYMER AND A PYRITHIONE SALT AND METHODS OF USING THE SAME

FIELD OF INVENTION

The present invention relates to certain compositions and processes useful for controlling the growth of one or more microorganisms. The present invention further relates to compositions and methods for preventing spoilage caused by microorganisms, such as bacteria, fungi, algae, and mixtures thereof, in various materials and media, particularly industrial materials and media. The novel processes and mixtures of the present invention show unexpected synergistic activity against microorganisms, including bacteria, fungi, algae, and mixtures thereof. The present invention particularly relates to the use of compositions/mixtures comprising an ionene polymer and a pyrithione salt.

BACKGROUND OF THE INVENTION

Many industrial materials and media, when wet or subjected to treatment in water, are susceptible to bacterial, fungal and/or algal deterioration or degradation unless steps are taken to inhibit such degradation or deterioration. These industrial materials and media include, but are not limited to, wood pulp, wood chips, lumber, adhesives, coatings, animal hides, paper mill liquors, pharmaceutical formulations, cosmetic and toiletry formulations, geological drilling lubricants, petrochemicals, agrochemical compositions, paints, leathers, wood, metalworking fluids, cooling water, recreational water, influent plant water, waste water, pasteurizers, retort cookers, tanning liquor, starch, proteinaceous materials, acrylic latex paint emulsions, and textiles.

To control deterioration or degradation caused by microorganisms, various industrial microbicides are used. Workers in the trade have continued to seek improved biocides that have low toxicity and are capable of exhibiting a prolonged biocidal effect against a wide variety of microorganisms at normal use.

For example, British Patent No. 1,390,004, incorporated herein in its entirety by reference, describes a biocidal composition for laundering textile fabrics containing a mixture of a heavy salt of a 2-mercapto-pyridine-N-oxide compound and a monomeric quaternary ammonium compound having the formula

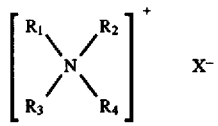

wherein at least one of the R groups in the above formula is or contains an alkyl group, an aralkyl group, an alkylaryl group or an amide derivative of such a group and contains from 6 to 26 carbon atoms; the remaining R groups are selected from alkyl, aryl, aralkyl, and alkylaryl groups and amide derivatives of such groups and contain from 1 to 26 carbon atoms; with the proviso that two R groups may combine with the N atom to form an imidazoline ring structure; and X is a halogen anion or an alkyl sulfate anion having from 1 to 4 carbon atoms.

Ionene polymers, i.e., cationic polymers containing quaternary nitrogens in the polymer backbone, is one group of biocides used in controlling bacteria and algae in various aqueous systems. Illustrative examples of these polymers and their uses are described in U.S. Pat. Nos. 3,874,870; 3,898,336; 3,931,319; 4,027,020; 4,054,542; 4,089,977; 4,111,679; 4,506,081; 4,581,058; 4,778,813; 4,970,211; 5,051,124; and 5,093,078, the disclosures of all of which are specifically incorporated by reference herein.

The use of pyrithiones and their metal derivatives to control microorganisms has also been described in, for example, U.S. Pat. Nos. 2,809,971 and 3,236,733, both incorporated in their entirety herein by reference. Although generally acceptable microbicides, the pyrithiones are expensive. Systems requiring high concentrations of pyrithione salts, therefore, are generally uneconomical.

Accordingly, there is a need in the art for a microbicidal composition that overcomes these and other problems.

SUMMARY OF THE INVENTION

It is therefore an object of this invention to provide a microbicidal composition capable of controlling the growth of at least one microorganism, particularly fungi, bacteria, algae, or mixtures thereof over prolonged periods of time. It is an additional object to preferably provide such compositions which are economical to use. Methods of controlling the growth of at least one microorganism are also objects of this invention.

In accordance with these and other objects, the present invention provides a composition comprising an ionene polymer and a pyrithione salt where the components are present in a combined amount synergistically effective to control the growth of at least one microorganism.

The present invention also provides a method for controlling the growth of at least one microorganism in or on a material or medium susceptible to attack by the microorganism. This method includes the step of adding to the material or medium a composition of the present invention in an amount synergistically effective to control the growth of the microorganism. The synergistically effective amount varies in accordance with the material or medium to be treated and can, for a particular application, be routinely determined by one skilled in the art in view of the disclosure provided herein.

The present invention also embodies the separate addition of an ionene polymer and a pyrithione salt to the products, materials, or media described above. According to this embodiment, the components are individually added to the system so that the final amount present at the time of use is that amount synergistically effective to control the growth of at least one microorganism.

The compositions of the present invention are also useful in preserving or controlling the growth of at least one microorganism in various types of industrial media or materials susceptible to attack by microorganisms. Such media or materials include but are not limited to dyes, pastes, lumber, leathers, textiles, pulp, wood chips, tanning liquor, paper mill liquor, polymer emulsions, paints, paper and other coating and sizing agents, metalworking fluids, geological drilling lubricants, petrochemicals, cooling water systems, recreational water, influent plant water, waste water, pasteurizers, retort cookers, pharmaceutical formulations, cosmetic and toiletry formulations, and the like.

The composition can also be useful in agrochemical formulations for the purpose of protecting seeds or crops against microbial spoilage.

Additional objects and advantages of the present invention will be set forth in part in the description which follows, and in part will be apparent from the description, or may be learned by the practice of the present invention. The objects and advantages of the present invention may be realized and obtained by means of the elements and combinations particularly pointed out in the claims.

It is to be understood that both the foregoing general description and the following detailed description are exemplary and explanatory only and are not restrictive of the present invention as claimed.

DETAILED DESCRIPTION OF PREFERRED EMBODIMENTS

The present invention provides a composition to control the growth of at least one microorganism comprising a mixture of an ionene polymer and a pyrithione salt where the components are present in a combined amount synergistically effective to control the growth of at least one microorganism. The composition preferably provides superior microbicidal activity at low concentrations against a wide range of microorganisms.

The compositions of the present invention can be used in a method for controlling the growth of at least one microorganism in or on a material or medium susceptible to attack by the microorganism. This method includes the step of adding to the material or medium a composition of the present invention, where the components of the composition are present in synergistically effective amounts to control the growth of the microorganism.

The synergistically effective amount varies in accordance with the material or medium to be treated and can, for a particular application, be routinely determined by one skilled in the art in view of this disclosure.

In lieu of adding the composition of the present invention to a material or medium to be treated, the ionene polymer and the pyrithione salt can be separately added to the material or medium to be treated. These components are individually added so that the final amount of the mixture of ionene polymer and pyrithione salt at the time of use is that amount synergistically effective to control the growth of at least one microorganism.

As stated earlier, the compositions of the present invention are useful in preserving various type of industrial products, media, or materials susceptible to attack by at least one microorganism. The compositions of the present invention are also useful in agrochemical formulations for the purpose of protecting seeds or crops against microbial spoilage. These methods of preserving and protecting are accomplished by adding the composition of the present invention to the products, media, or materials in an amount synergistically effective to preserve the products, media, or materials from attack by at least one microorganism or to effectively protect the seeds or crops against microbial spoilage.

According to the methods of the present invention, controlling or inhibiting the growth of at least one microorganism includes the reduction and/or the prevention of such growth.

It is to be further understood that by "controlling" (i.e., preventing) the growth of at least one of microorganism, the growth of the microorganism is inhibited. In other words, there is no growth or essentially no growth of the microorganism. "Controlling" the growth of at least one microorganism maintains the microorganism population at a desired level, reduces the population to a desired level (even to undetectable limits, e.g., zero population), and/or inhibiting the growth of the microorganism. Thus, in one embodiment of the present invention, the products, material, or media susceptible to attack by the at least one microorganism are preserved from this attack and the resulting spoilage and other detrimental effects caused by the microorganism.

Further, it is also to be understood that "controlling" the growth of at least one microorganism also includes biostatically reducing and/or maintaining a low level of at least one microorganism such that the attack by the microorganism and any resulting spoilage or other detrimental effects are mitigated, i.e., the microorganism growth rate or microorganism attack rate is slowed down and/or eliminated.

When two chemical microbicides are mixed and added to the product or added separately three results are possible:

1) The chemicals in the product would produce an additive (neutral) effect,
2) The chemicals in the product would produce an antagonistic effect, or
3) The chemicals in the product would produce a synergistic effect.

An additive effect has no economic advantage over the individual components. The antagonistic effect would produce a negative impact. Only a synergistic effect, which is less likely than either an additive or antagonistic effect, would produce a positive effect and therefore possess economic advantages.

It is known in the microbicidal literature that there is no theoretical method to anticipate additive, antagonistic, or synergistic effects when two biocides are mixed to yield a new formulation. Nor is there a method to predict the relative proportions of the different biocides required to produce one of the three effects described above.

The inventive microbicidal compositions combining an ionene polymer and a pyrithione salt demonstrate an unexpected synergistic effect compared to the respective components alone. Thus, these compositions achieve superior, i.e. greater than additive, microbicidal activity, preferably even at low concentrations, against a wide variety of microorganisms. Examples of these microorganisms include fungi, bacteria, algae, and mixtures thereof such as, but not limited to, *Trichoderma harzianun*, *Pseudomonas aeruginosa*, and *Chlorella pyrenoidosa*. Preferably, the compositions of the present invention have a low toxicity.

Ionene polymers may be classified according to the repeating unit found in the polymer. This repeating unit results from the reactants used to make the ionene polymer.

A first type of ionene polymer that can be used in the present invention comprises the repeating unit of formula I:

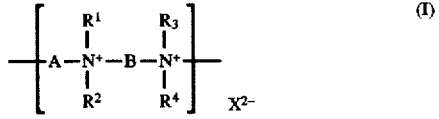

wherein $R^1$, $R^2$, $R^3$, and $R^4$ can be identical or different, and are selected from hydrogen, $C_1$–$C_{20}$ alkyl, or benzyl. Each $C_1$–$C_{20}$ alkyl can be unsubstituted or substituted, for instance, optionally substituted with at least one hydroxyl group. Each benzyl can also be unsubstituted or substituted, for instance, optionally substituted on the benzene moiety with at least one $C_1$–$C_{20}$ alkyl group. Preferably, $R^1$, $R^2$, $R^3$ and $R^4$ are all methyl or ethyl.

The group "A" is a divalent radical selected from $C_1$–$C_{10}$ alkyl, $C_2$–$C_{10}$ alkenyl $C_2$–$C_{10}$ alkynyl, $C_1$–$C_{10}$ hydroxyalkyl, symmetric or asymmetric di-$C_1$–$C_{10}$-alkylether, aryl, aryl-$C_1$–$C_{10}$-alkyl, or $C_1$–$C_{10}$-alkylaryl-$C_1$–$C_{10}$ alkyl. The group "A" can be unsubstituted or substituted. Preferably, "A" is $C_1$–$C_5$ alkyl, $C_2$–$C_5$ alkenyl, $C_2$–$C_5$ hydroxyalkyl, or symmetric di-$C_2$–$C_5$-alkylether. Most preferably "A" is propylene, 2-hydroxypropylene, or diethylene ether.

The group "B" is a divalent radical, which can be the same as the group "A," is selected from $C_1$–$C_{10}$ alkyl, $C_2$–$C_{10}$ alkenyl, $C_2$–$C_{10}$ alkynyl, $C_1$–$C_{10}$ hydroxyalkyl, symmetric or asymmetric di-$C_1$-$C_{10}$-alkylether, aryl, aryl-$C_1$-$C_{10}$-alkyl, or $C_1$-$C_{10}$-alkylaryl-$C_1$-$C_{10}$-alkyl. The group "B" can be unsubstituted or substituted. Preferably, "B" is $C_1$-$C_5$ alkyl, $C_2$-$C_5$alkenyl, $C_2$-$C_5$ hydroxyalkyl, aryl, aryl-$C_1C_5$-alkyl, or $C_1$-$C_5$ alkylaryl-$C_1$-$C_5$ alkyl. Most preferably "B" is ethylene, propylene, butylene, or hexamethylene.

The counter ion, $X^{2-}$, is a divalent counter ion, two monovalent counter ions or a fraction of a polyvalent counter ion sufficient to balance the cationic charge in the repeating unit which forms the ionene polymer backbone. Preferably, $X^{2-}$ is two monovalent anions selected from a halide anion and a trihalide anion and more preferably, chloride or bromide. Ionene polymers having trihalide counter ions are described, for example, in U.S. Pat. No. 3,778,476, the disclosure of which is specifically incorporated herein by reference.

Ionene polymers having the repeating unit of formula I may be prepared by any of the methods known to the art. One such method is to react a diamine of the formula $R^1R^2N$—B—$NR^3R^4$ with a dihalide of the formula X—A—X, wherein the substituents $R^1$, $R^2$, $R^3$, $R^4$, A, X, and B have the same meanings as in formula (I). Ionene polymers having this repeating unit and methods for their preparation are described, for example, in U.S. Pat. Nos. 3,874,870; 3,931,319; 4,025,627; 4,027,020; 4,506,081; and 5,093,078, the disclosures of all of which are incorporated herein by reference. The biological activity of ionene polymers having the repeating unit of formula I is also described in these patents.

A second type of ionene polymer that can be used in the present invention comprises the repeating unit of formula II:

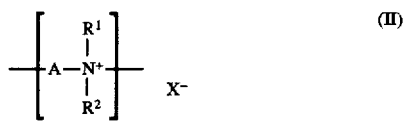

wherein $R^1$, $R^2$, and A are as defined above for formula (I). $X^-$ is a monovalent counter ion, one-half of a divalent counter ion or a fraction of a polyvalent counter ion sufficient to balance the cationic charge of the repeating unit which forms the ionene polymer. $X^-$ may be, for example, a halide, or trihalide anion and is preferably chloride or bromide.

Ionene polymers having the repeating unit of formula (II) may also be prepared by any of the known methods. One method is to react an amine of the formula $R^1R^2N$ with a haloepoxide such as epichlorohydrin, wherein $R^1$ and $R^2$ have the same meanings as in formula (I). Ionene polymers having the repeating unit of formula (II) are, for example, described in U.S. Pat. Nos. 4,111,679 and 5,051,124, the disclosures of which are incorporated herein by reference. The biological activity of ionene polymers having the repeating unit of formula (II) is also described in these patents.

A third type of ionene polymer that can be used in the present invention comprises a repeating unit of formula (III):

$+R—B'+$ (III)

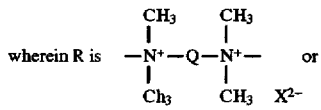

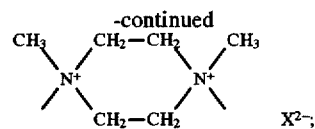

Q is $-(CHR')_p-$, $-CH_2-CH=CH-CH_2-$, $-CH_2-CH_2-O-CH_2-CH_2-$, $-CH_2-CH(OH)-CH_2-$, or

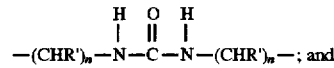

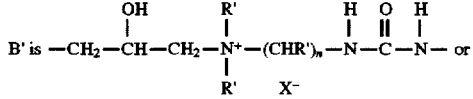

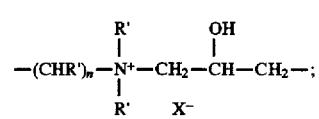

wherein n and p are integers and independently vary from 2 to 12; each R' is independently hydrogen or a lower alkyl group (e.g., $C_1$-$C_{12}$ alkyl) wherein the alkyl group is unsubstituted or substituted; $X^{2-}$ is a divalent counter ion, two monovalent counter ions or a fraction of a polyvalent counter ion sufficient to balance the cationic charge in the group R; and $X^-$ is a monovalent counter ion, one-half of a divalent counter ion or a fraction of a polyvalent counter ion sufficient to balance the cationic charge in the group B'.

Preferably, R' is hydrogen or a $C_1$-$C_4$ alkyl; n is 2–6 and p is 2–6. Most preferably, R' is hydrogen or methyl, n is 3 and p is 2. Preferred counter ions, $X^{2-}$ and $X^-$ are the same as those discussed above with respect to formulae (I) and (II).

The polymers of formula (III) may be derived from bis(dialkylaminoalkyl) ureas, which are also known as urea diamines, by known methods. Ionene polymers of formula (III), methods of their preparation, and their biological activities are, for example, described in U.S. Pat. No. 4,506,081; the disclosure of which is incorporated herein by reference.

Ionene polymers comprising the repeating units of formulae (I), (II), and (III) may also be cross-linked with primary, secondary, or other polyfunctional amines using means known in the art. Ionene polymers can be cross-linked either through the quaternary nitrogen atom or through another functional group attached to the polymer backbone or to a side chain.

Cross-linked ionene polymers, prepared using cross-linking coreactants, are disclosed in U.S. Pat. No. 3,738,945 and Reissue U.S. Pat. No. 28,808, the disclosures of which are incorporated herein by reference. The Reissue Patent describes the cross-linking of ionene polymers prepared by the reaction of dimethylamine and epichlorohydrin. The cross-linking coreactants listed are ammonia, primary amines, alkylenediamines, polyglycolamines, piperazines, heteroaromatic diamines, and aromatic diamines.

U.S. Pat. No. 5,051,124, the disclosure of which is incorporated herein by reference, describes cross-linked ionene polymers resulting from the reaction of dimethylamine, a polyfunctional amine, and epichlorohydrin. Methods of inhibiting the growth of microorganisms using such cross-linked ionene polymers are also described.

Other examples of various cross-linked ionene polymers and their properties are provided in U.S. Pat. Nos. 3,894,946, 3,894,947, 3,930,877, 4,104,161, 4,164,521, 4,147,627, 4,166,041, 4,606,773, and 4,769,155. The disclosures of each of these patents is incorporated herein by reference.

The ionene polymers comprising the repeating units of formulae (I), (II), or (III) may also be capped, i.e., have a specific end group. Capping may be achieved by any means known in the art. For example, an excess of one of the reactants used to make the ionene polymer can be employed to provide a capping group. Alternatively, a calculated quantity of a monofunctional tertiary amine or monofunctional substituted or unsubstituted alkyl halide can be reacted with an ionene polymer to obtain a capped ionene polymer. Ionene polymers can be capped at one or both ends. Capped ionene polymers and their microbicidal properties are described in U.S. Pat. Nos. 3,931,319 and 5,093,078, the disclosures of each of these patents is incorporated herein by reference.

The specific ionene polymer employed is preferably selected based on the compatibility with the medium of intended use. Compatibility is determined by criteria such as solubility in the fluid system and lack of reactivity with the fluid or material or media in question. The compatibility is readily determined by one of ordinary skill by adding the ionene polymer to the material or media to be used. When used in a fluid system it is preferable that the ionene polymer be freely soluble in the particular fluid resulting in a uniform solution or dispersion.

Among the ionene polymers discussed above, a particularly preferred ionene polymer having a repeating unit of formula (I) is poly[oxyethylene(dimethyliminio)ethylene (di-methyliminio)ethylene dichloride]. In this ionene polymer, $R^1$, $R^2$, $R^3$ and $R^4$ are each methyl, A is —$CH_2CH_2OCH_2CH_2$—, B is —$CH_2CH_2$—, and $X^{2-}$ is $2Cl^-$, and the average molecular weight is 1,000–5,000. This ionene polymer is available from Buckman Laboratories, Inc. of Memphis, Tenn. as Busan® 77 product, a 60% aqueous dispersion of the polymer, or WSCP® product, a 60% aqueous dispersion of the polymer. Busan® 77 and WSCP® products are biocides used primarily in aqueous systems, including metalworking fluids for microorganism control.

Another particularly preferred ionene polymer having a repeating unit of formula (I), also available from Buckman Laboratories, Inc. as Busan® 79 product, or WSCP II product is the ionene polymer where $R^1$, $R^2$, $R^3$ and $R^4$ are each methyl, A is —$CH_2CH(OH)CH_2$—, B is —$CH_2CH_2$—, and $X^{2-}$ is $2Cl^-$. This ionene polymer is a reaction product of N,N,N',N'-tetramethyl-1,2-ethanediamine, with (chloromethyl)-oxirane, and has a 1,000–5,000 average molecular weight. The polymer product Busan® 79 or WSCP II product is a 60% aqueous solution of the polymer.

Preferred ionene polymers having the repeating unit of formula (II) are those where $R^1$ and $R^2$ are each methyl, A is —$CH_2CH(OH)CH_2$—, and $X^-$ is $Cl^-$. Busan® 1055 product is a 50% aqueous dispersion of such an ionene polymer obtained as a reaction product of dimethylamine with (chloromethyl)oxirane having a 2,000–10,000 average molecular weight.

Busan® 1157 product is a 50% aqueous dispersion of the ionene polymer having the repeating unit of formula (II), obtained as a reaction product of dimethylamine with epichlorohydrin, cross-linked with ethylenediamine, where $R^1$ and $R^2$ are each methyl, A is —$CH_2CH(OH)CH_2$— and $X^-$ is $Cl^-$. This ionene polymer has a 100,000–500,000 average molecular weight.

Busan® 1155 product is a 50% aqueous dispersion of an ionene polymer having the repeating unit of formula (II), where $R^1$ and $R^2$ are each methyl, A is —$CH_2CH(OH)$ $CH_2$—, $X^-$ is $Cl^-$ and the ionene polymer is cross-linked with ammonia. This ionene polymer has a molecular weight of approximately 100,000–500,000.

Busan® 1099 product or Bubond® 65 product is a 25% aqueous dispersion of a cross-linked ionene polymer having repeating units of formula (II), where $R^1$ and $R^2$ are each methyl, A is —$CH_2CH(OH)CH_2$—, $X^-$ is $Cl^-$, the cross-linking agent is monomethylamine. This ionene polymer has a molecular weight of approximately 10,000–100,000.

Preferred ionene polymers having the repeating unit of formula (III) are those where R is a urea diamine and $X^{2-}$ is $2Cl^-$, B' is $CH_2CH(OH)CH_2$, and $X^-$ is $Cl^-$. BL® 1090 is a 50% aqueous dispersion of the ionene polymer obtained as a reaction product of N,N'-bis-[1-(3-(dimethylamino)-propyl]urea and epichlorohydrin, such an ionene polymer having a 2,000–15,000, preferably 3,000–7,000, average molecular weight.

Each of the above ionene polymers and products identified by trade name is available from Buckman Laboratories, Inc. of Memphis, Tenn.

The pyrithione salt is preferably a metal salt of pyrithione. More preferably, the pyrithione salt is a Group I, II, or III metal salt, such as sodium pyrithione, magnesium pyrithione, zinc pyrithione, copper pyrithione, or aluminum pyrithione. These salts are known to the art and are commercially available or can be readily prepared from available materials using known methods.

For example, sodium pyrithione and zinc pyrithione are commercially available and their preparations are described in U.S. Pat. Nos. 3,159,640 and 2,809,971, respectively, and both disclosures are incorporated in their entirety herein by reference. These preparations are supplied either as a solid, liquid, or dispersion. One such commercial formulations of sodium pyrithione is a 40% aqueous solution known as Sodium Omadine. A 48% dispersion of zinc pyrithione is also available as Zinc Omadine.

The particular pyrithione salt employed may be selected based on the compatibility of these compounds with the materials or media. Compatibility is determined by criteria such as solubility in the fluid system and lack of reactivity with the fluid or material or media in question. The compatibility is readily determined by one of ordinary skill by adding the pyrithione salt to the material or media to be used. When used in a fluid system it is preferable that the pyrithione salt be freely soluble in the particular fluid resulting in a uniform solution or dispersion.

As described above, components (a) an ionene polymer and (b) a pyrithione salt are used in synergistically effective amounts. The weight ratios of (a) to (b) vary depending on the type of microorganisms and material or media to which the composition is applied. In view of the present invention, one skilled in the art can readily determine without undue experimentation, the appropriate weight ratios for a specific application. The ratio of component (a) to component (b) preferably ranges from 1:99 to 99:1, more preferably from 1:30 to 30:1, and most preferably 1:2 to 2:1.

Depending upon the specific application, the composition may be prepared in liquid form by dissolving the composition in water or in an organic solvent, or in dry form by adsorbing onto a suitable vehicle or it can be compounded into a tablet form. The preservative containing the composition of the present invention may be prepared in an emulsion form by emulsifying it in water, or if necessary, by adding a surfactant. Additional chemicals, such as insecticides, may be added to the foregoing preparations depending upon the intended use of the preparation.

The mode as well as the rates of application of the composition of this invention could vary depending upon the intended use. The composition could be applied by spraying or brushing onto the material or product. The material or product in question could also be treated by dipping in a suitable formulation of the composition. In a liquid or liquid-like medium, the composition could be added into the medium by pouring, or by metering with a suitable device so that a solution or a dispersion of the composition could be produced.

The synergistic activity of the combinations described above has been confirmed using standard laboratory techniques as illustrated below. The following examples are intended to illustrate, not limit, the present invention.

MICROBIOLOGICAL EVALUATION

A. Fungal evaluation

Mineral salts-glucose medium was used. To prepare the medium, the following ingredients were added to 1 liter of deionized water: 0.7 g of $KH_2PO_4$, 0.7 g of $MgSO_4.7H_2O$, 1.0 g of $NH_4NO_3$, 0.005 g of $NaCl$, 0.002 g of $FeSO_4.7H_2O$, 0.002 g of $ZnSO_4.7H_2O$, 0.001 g of $MnSO_4.7H_2O$, 10 g of Glucose. The pH of the medium was adjusted to 6 with 1N NaOH. The medium was distributed in 5 mL amounts in test tubes and autoclaved at 121° C. for 20 minutes. The fungus, *Trichoderma harzianum* was grown on a potato dextrose agar slant for 7 to 10 days and a spore suspension prepared by washing down the spores from the plant into a sterile saline solution. After addition of the biocides in the desired concentrations to the sterile mineral salts-glucose medium, the fungal spore suspension was added. The final spore concentration was approximately $10^6$ cfu/mL. The inoculated media was incubated at 28° C. for 14 days.

B. Bacterial evaluation

Nutrient broth (2.5 g/liter of deionized water) was prepared. The pH was 6.8. This was distributed in 5 mL amounts in test tubes and autoclaved for 20 minutes at 121° C. After addition of the biocides in the desired concentrations to the nutrient broth, 100 microliters of a suspension of *Pseudomonas aerugnosa* cells of approximately $9.3 \times 10^8$ cfc/mL were added and incubated at 37° C. for 48 hours.

An algae broth was prepared by dissolving the following ingredients in 1 liter of deionized water: 1.0 g of $NaNO_3$, 50 mg of $NH_4Cl$, 58 mg of $CaCl$, 0.513 g of $MgSO_4$, 0.25 g $K_2HPO_4$, 3.0 mg $FeCl_3.6H_2O$. The medium was distributed in 50 g amounts and autoclaved at 121° C. for 20 minutes. After autoclaving, the biocides were added to the broth in the desired concentrations. Then one milliliter of a two-week old culture of *Chlorella pyrenoidosa* was added and incubated at a temperature of 25° C. to 28° C. and lighting of 180 ft.-candle intensity (12 hr. light; 12 hr. darkness) for 28 days.

In examples 1 and 2 synergism was demonstrated in separate experiments by testing combinations of the ionene polymer poly[oxyethylene(dimethyliminio)ethylene (dimethyl-iminio)ethylene dichloride] or poly [hydroxyethylene-(dimethyliminio)-2-hydroxypropylene (dimethyliminio)-methylene dichloride] (designated component A) and sodium pyridinethiol-1-oxide (designated component B) in a series of tests in varying ratios and a range of concentrations against the fungus *Trichoderma harzianum*, the bacterium *Pseudomonas aeruginosa* and the algae *Chlorella pyrenoidosa* using the methods described above.

The lowest concentration of each mixture or compound which completely prevented growth of the fungi for two weeks, the algae for four weeks, and the bacteria for 48 hours was taken as the end points for synergism calculations. End points for the various mixtures were then compared with the end points for the pure active ingredients alone in concomitantly prepared flasks or test tubes.

Synergism was demonstrated by the method described by Kull, E. C., Eisman, P. C., Sylwestrwicz, H. D., and Mayer, R. L., *Applied Microbiology* 9: 538–541 (1961):

QA/Qa+QB/Qb wherein

Qa=Concentration of compound A in parts per million, acting alone, which produced an end point.

Qb=Concentration of compound B in parts per million, acting alone, which produced an end point.

QA=Concentration of compound A in parts per million, in the mixture, which produced an end point.

QB=Concentration of compound B in parts per million, in the mixture, which produced an end point.

When the sum of QA/Qa and QB/Qb is greater than one, antagonism is indicated and when the sum is equal to one, additivity is indicated. When the sum of this value is less than one, synergism exists.

This procedure for demonstrating synergism of the compositions of this invention is a widely used and acceptable procedure. More detailed information is provided in the article by Kull et al. Further information concerning this procedure is contained in U.S. Pat. No. 3,231,509, the disclosure of which is herein incorporated by reference.

Based on the above criteria, a synergistic activity against bacteria, fungi, algae, and mixtures thereof is observed when an ionene polymer is combined with a pyrithione salt. Examples showing synergistic results can be found in Tables 1 and 2.

In general, however, an effective fungicidal, bactericidal, or algicidal response can be obtained when the synergistic combination is employed in concentrations ranging from about 0.01 ppm to 1% by weight (i.e., 10,000 ppm) of the ionene polymer, preferably 0.1 to 5000 ppm, and most preferably 0.1 ppm to 1000 ppm; and from about 0.01 to about 5000 ppm of the pyrithione salt, preferably 0.1 to 2000 ppm, and most preferably 0.1 to 1000 ppm.

EXAMPLE 1

Component A = Poly[oxyethylene(dimethyl-iminio)ethylene(dimethyliminio)ethylene dichloride]
Component B = Sodium pyrithione

| Test organism | Quantities producing end points (ppm) | | | | | | |
|---|---|---|---|---|---|---|---|
| | $Q_a$ | $Q_A$ | $Q_b$ | $Q_B$ | $Q_A/Q_a$ | $Q_B/Q_b$ | $Q_AQ_a + Q_B/Q_b$ |
| *Trichoderma harzianum* | >1200 | — | — | — | — | — | — |
| | — | 30 | — | 2 | 0.03 | 0.2 | 0.23 |
| | — | 60 | — | 2 | 0.05 | 0.2 | 0.25 |
| | — | 150 | — | 2 | 0.13 | 0.2 | 0.33 |
| | — | 300 | — | 2 | 0.25 | 0.2 | 0.45 |
| | — | 600 | — | 2 | 0.5 | 0.2 | 0.7 |
| | — | 15 | — | 4 | 0.01 | 0.4 | 0.41 |
| | — | 30 | — | 4 | 0.03 | 0.4 | 0.43 |
| | — | 60 | — | 4 | 0.05 | 0.4 | 0.45 |
| | — | 150 | — | 4 | 0.13 | 0.4 | 0.53 |
| | — | 300 | — | 4 | 0.25 | 0.4 | 0.65 |
| | — | 600 | — | 4 | 0.5 | 0.4 | 0.9 |
| | — | — | 10 | — | — | — | — |
| *Pseudomonas aeruginosa* | 6 | — | — | — | — | — | — |
| | — | 1.5 | — | 40 | 0.25 | 0.5 | 0.75 |
| | — | 3 | — | 4 | 0.5 | 0.05 | 0.55 |
| | — | 3 | — | 15 | 0.5 | 0.19 | 0.69 |
| | — | 3 | — | 30 | 0.5 | 0.38 | 0.88 |
| | — | — | 80 | — | — | — | — |
| *Chlorella* | 1.5 | — | — | — | — | — | — |

11

-continued

Component A = Poly[oxyethylene(dimethyl-
iminio)ethylene(dimethyliminio)ethylene dichloride]
Component B = Sodium pyrithione Quantities producing end points (ppm)

| Test organism | $Q_a$ | $Q_A$ | $Q_b$ | $Q_B$ | $Q_A/Q_a$ | $Q_B/Q_b$ | $Q_AQ_a + Q_B/Q_b$ |
|---|---|---|---|---|---|---|---|
| pyrenoidosa | — | 0.38 | — | 0.1 | 0.25 | 0.03 | 0.28 |
| | — | — | 4 | — | — | — | — |

EXAMPLE 2

Component A = Poly[hydroxyethylene(dimethyl-
iminio)ethylene(dimethyliminio)methylene dichloride].
Component B = Sodium pyrithione Quantities producing end points (ppm)

| Test organism | $Q_a$ | $Q_A$ | $Q_b$ | $Q_B$ | $Q_A/Q_a$ | $Q_B/Q_b$ | $Q_AQ_a + Q_B/Q_b$ |
|---|---|---|---|---|---|---|---|
| Trichoderma harzianum | >1200 | — | — | — | — | — | — |
| | — | 15 | — | 2 | 0.01 | 0.2 | 0.21 |
| | — | 30 | — | 2 | 0.02 | 0.2 | 0.22 |
| | — | 60 | — | 2 | 0.04 | 0.2 | 0.24 |
| | — | 150 | — | 2 | 0.1 | 0.2 | 0.3 |
| | — | 300 | — | 2 | 0.25 | 0.2 | 0.45 |
| | — | 600 | — | 2 | 0.5 | 0.2 | 0.7 |
| | — | 15 | — | 4 | 0.01 | 0.4 | 0.41 |
| | — | 30 | — | 4 | 0.02 | 0.4 | 0.42 |
| | — | 60 | — | 4 | 0.04 | 0.4 | 0.44 |
| | — | 150 | — | 4 | 0.1 | 0.4 | 0.5 |
| | — | 300 | — | 4 | 0.25 | 0.4 | 0.65 |
| | — | 600 | — | 4 | 0.5 | 0.4 | 0.9 |
| | — | — | 10 | — | — | — | — |
| Pseudomonas aeruginosa | 15 | — | — | — | — | — | — |
| | — | 0.6 | — | 40 | 0.04 | 0.5 | 0.54 |
| | — | 1.5 | — | 40 | 0.1 | 0.5 | 0.6 |
| | — | 3 | — | 40 | 0.2 | 0.5 | 0.7 |
| | — | 6 | — | 2 | 0.4 | 0.03 | 0.43 |
| | — | 6 | — | 4 | 0.4 | 0.05 | 0.45 |
| | — | 6 | — | 10 | 0.4 | 0.13 | 0.53 |
| | — | 6 | — | 20 | 0.4 | 0.25 | 0.65 |
| | — | 6 | — | 40 | 0.4 | 0.5 | 0.9 |
| | — | — | 80 | — | — | — | — |
| Chlorella pyrenoidosa | 6 | — | — | — | — | — | — |
| | — | 0.75 | — | 0.2 | 0.13 | 0.05 | 0.18 |
| | — | — | 4 | — | — | — | — |

Other embodiments of the present invention will be apparent to those skilled in the art from consideration of the specification and practice of the invention disclosed herein. It is intended that the specification and examples be considered exemplary only, with a true scope and spirit of the invention being indicated by the following claims.

What is claimed is:

1. A composition comprising (a) an ionene polymer and (b) a pyrithione salt, wherein components (a) and (b) are present in a synergistically microbicidally effective combined amount to control the growth of at least one microorganism, wherein the ionene polymer comprises the repeating unit of formula I:

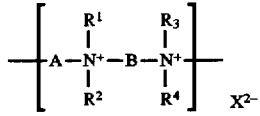

wherein $R^1$, $R^2$, $R^3$, and $R^4$ are identical or different, and are selected from hydrogen, $C_1$–$C_{20}$, alkyl optionally substituted with at least one hydroxyl group, or benzyl optionally substituted on the benzene moiety with at least one $C_1$–$C_{20}$, alkyl group;

A is a divalent radical selected from $C_1$–$C_{10}$ alkyl, $C_2$–$C_{10}$ alkenyl, $C_2$–$C_{10}$ alkynyl, $C_1$–$C_{10}$ hydroxyalkyl, symmetric or asymmetric di-$C_1$–$C_{10}$-alkylether, aryl, aryl-$C_1$–$C_{10}$-alkyl, or $C_1$–$C_{10}$-alkylaryl-$C_1$–$C_{10}$ alkyl;

B is a divalent radical selected from $C_1$–$C_{10}$ alkyl, $C_2$–$C_{10}$ alkenyl, $C_2$–$C_{10}$ alkynyl, $C_1$–$C_{10}$ hydroxyalkyl, symmetric or asymmetric di-$C_1$–$C_{10}$-alkylether, aryl, aryl-$C_1$–$C_{10}$-alkyl, or $C_1$–$C_{10}$-alkylaryl-$C_1$–$C_{10}$-alkyl; and $X^{2-}$ is a divalent counter ion, two monovalent counter ions, or a fraction of a polyvalent counter ion sufficient to balance the cationic charge in the repeating unit which forms the ionene polymer backbone.

2. The composition of claim 1, wherein the microorganism is selected from bacteria, fungi, algae, or mixtures thereof.

3. The composition of claim 1, wherein the $C_1$–$C_{20}$ alkyl is substituted with at least one hydroxyl group.

4. The composition of claim 1, wherein benzyl is substituted on the benzene moiety with at least one $C_1$–$C_{20}$ alkyl group.

5. The composition of claim 1, wherein the ionene polymer is capped or cross-linked.

6. The composition of claim 1, wherein the pyrithione salt is a Group I, II, or III metal salt of pyrithione.

7. The composition of claim 6, wherein the pyrithione salt is sodium pyrithione, zinc pyrithione, copper pyrithione, aluminium pyrithione, or magnesium pyrithione.

8. The composition of claim 1, wherein the weight ratio of (a) to (b) is from about 1:99 to about 99:1.

9. The composition of claim 8, wherein the weight ratio of (a) to (b) is from about 1.30 to about 30:1.

10. The composition of claim 9, wherein the weight ratio of (a) to (b) is from about 1:2 to about 2:1.

11. The composition of claim 1, wherein $R^1$, $R^2$, $R^3$ and $R^4$ are each methyl, A is —$CH_2CH_2OCH_2CH_2$—, B is —$CH_2CH_2$—, and $X^{2-}$ is 2Cl$^-$.

12. The composition of claim 1, wherein $R^1$, $R^2$, $R^3$ and $R^4$ are each methyl, A is —$CH_2CH(OH)CH_2$—, B is —$CH_2CH_2$—, and $X^{2-}$ is 2Cl$^-$.

13. The composition of claim 1, wherein $R^1$, $R^2$, $R^3$ and $R^4$ are different.

14. The composition of claim 1, wherein $R^1$, $R^2$, $R^3$ and $R^4$ are the same.

15. The composition of claim 1, wherein A is a $C_1$–$C_{20}$ alkyl and B is a $C_1$–$C_{10}$ alkyl.

16. The composition of claim 1, wherein A is a $C_2$–$C_{10}$ alkenyl.

17. The composition of claim 1, wherein B is a $C_2$–$C_{10}$ alkenyl.

18. The composition of claim 1, wherein A is a $C_2$–$C_{10}$ alkynyl and B is a $C_2$–$C_{10}$ alkynyl.

19. A method of controlling the growth of at least one microorganism in or on a material or medium susceptible to attack by microorganism comprising the step of adding to the material or medium a composition comprising (a) an ionene polymer and (b) a pyrithione salt in a synergistically microbicidally effective combined amount to control the growth of at least one microorganism, wherein the ionene polymer comprises the repeating unit of formula I:

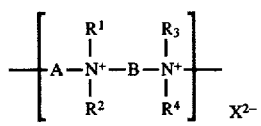

wherein

R$^1$, R$^2$, R$^3$, and R$^4$ are identical or different and are selected from hydrogen, C$_1$–C$_{20}$ alkyl optionally substituted with at least one hydroxyl group, or benzyl optionally substituted on the benzene moiety with at least one C$_1$–C$_{20}$ alkyl group;

A is a divalent radical selected from C$_1$–C$_{10}$ alkyl, C$_2$–C$_{10}$ alkenyl, C$_2$–C$_{10}$ alkynyl, C$_1$–C$_{10}$ hydroxyalkyl, symmetric or asymmetric di-C$_1$–C$_{10}$-alkylether, aryl, aryl-C$_1$–C$_{10}$-alkyl, or C$_1$–C$_{10}$-alkylaryl-C$_1$–C$_{10}$ alkyl;

B is a divalent radical selected from C$_1$–C$_{10}$ alkyl, C$_2$–C$_{10}$ alkenyl, C$_2$–C$_{10}$ alkynyl, C$_1$–C$_{10}$ hydroxyalkyl, symmetric or asymmetric di-C$_1$–C$_{10}$-alkylether, aryl, aryl-C$_1$–C$_{10}$-alkyl, or C$_1$–C$_{10}$-alkylaryl-C$_1$–C$_{10}$-alkyl; and X$^{2-}$ is a divalent counter ion, two monovalent counter ions or a fraction of a polyvalent counter ion sufficient to balance the cationic charge in the repeating unit which forms the ionene polymer backbone.

20. The method of claim 19, wherein the microorganism is selected from bacteria, fungi, algae, or mixtures thereof.

21. The method of claim 19, wherein the material or medium is wood pulp, wood chips, lumber, paints, leathers, adhesives, coatings, animal hides, tanning liquor, paper mill liquor, metalworking fluids, petrochemicals, pharmaceutical formulations, cooling water, recreational water, dyes, clays, mineral slurries, cationic surfactants, formulations with cationic surfactants, influent water, waste water, pasteurizers, retort cookers, cosmetic or toiletry formulations, textiles, geological, drilling lubricants, or agrochemical compositions for crop or seed protection.

22. The method of claim 19, wherein the material or medium is in the form of a solid, dispersion, emulsion, solution or a solid.

23. The composition of claim 19, wherein the C$_1$–C$_{20}$ alkyl is substituted with at least one hydroxyl group.

24. The composition of claim 19, wherein benzyl is substituted on the benzene moiety with at least one C$_1$–C$_{20}$ alkyl group.

25. The method of claim 19, wherein the pyrithione salt is a Group I, II, or III metal salt of pyrithione.

26. The method of claim 25, wherein the pyrithione salt is sodium pyrithione, zinc pyrithione, copper pyrithione, aluminium pyrithione, or magnesium pyrithione.

27. The method of claim 19, wherein the weight ratio of (a) to (b) is from about 1:99 to about 99:1.

28. The method of claim 27, wherein the weight ratio of (a) to (b) is from about 1:30 to about 30:1.

29. The method of claim 28, wherein the weight ratio of (a) to (b) is from about 1:2 to about 2:1.

30. The method of claim 19, wherein R$^1$, R$^2$, R$^3$ and R$^4$ are each methyl, A is —CH$_2$CH$_2$OCH$_2$CH$_2$—, B is —CH$_2$CH$_2$—, and X$^{2-}$ is 2Cl$^-$.

31. The method of claim 19, wherein R$^1$, R$^2$, R$^3$ and R$^4$ are each methyl, A is —CH$_2$CH(OH)CH$_2$—, B is —CH$_2$CH$_2$—, and X$^{2-}$ is 2Cl$^-$.

32. The method of claim 19, wherein R$^1$, R$^2$, R$^3$ and R$^4$ are different.

33. The method of claim 19, wherein R$^1$, R$^2$, R$^3$ and R$^4$ are the same.

34. The method of claim 19, wherein A is a C$_1$–C$_{20}$ alkyl and B is a C$_1$–C$_{10}$ alkyl.

35. The method of claim 19, wherein A is a C$_2$–C$_{10}$ alkynyl and B is a C$_2$–C$_{10}$ alkynyl.

36. A method for preventing spoilage of a material or medium caused by microorganism selected from bacteria, fungi, algae, or mixtures thereof comprising the step of adding to the material or medium a composition comprising (a) an ionene polymer and (b) a pyrithione salt in a synergistically microbicidally effective combined amount to prevent spoilage, wherein the ionene polymer comprises the repeating unit of formula I:

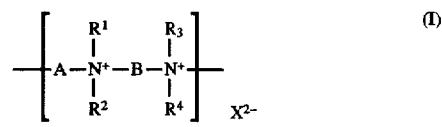

wherein

R$^1$, R$^2$, R$^3$, and R$^4$ are identical or different, and are selected from hydrogen, C$_1$–C$_{20}$ alkyl optionally substituted with at least one hydroxyl group, or benzyl optionally substituted on the benzene moiety with at least one C$_1$–C$_{20}$ alkyl group;

A is a divalent radical selected from C$_1$–C$_{10}$ alkyl, C$_2$–C$_{10}$ alkenyl, C$_2$–C$_{10}$ alkynyl, C$_1$–C$_{10}$ hydroxyalkyl, symmetric or asymmetric di-C$_1$–C$_{10}$-alkylether, symmetric or asymmetric di-C$_1$–C$_{10}$-alkylether, aryl, aryl-C$_1$–C$_{10}$-alkyl, or C$_1$–C$_{10}$-alkylaryl-C$_1$–C$_{10}$-alkyl;

B is a divalent radical selected from C$_1$–C$_{10}$ alkyl, C$_2$–C$_{10}$ alkenyl, C$_2$–C$_{10}$ alkynyl, C$_1$–C$_{10}$ hydroxyalkyl, symmetric or asymmetric di-C$_1$–C$_{10}$-alkylether, aryl, aryl-C$_1$–C$_{10}$-alkyl, or alkylaryl-C$_1$–C$_{10}$-alkyl; and X$^{2-}$ is a divalent counter ion, two monovalent counter ions, or a fraction of a polyvalent counter ion sufficient to balance the cationic charge in the repeating unit which forms the ionene polymer backbone.

37. The method of claim 36, wherein the material is seeds or crops.

38. The method of claim 36, wherein the components (a) and (b) are added separately to the material or medium.

39. The method of claim 36, wherein the pyrithione salt is a Group I, II, or III metal salt of pyrithione.

40. The method of claim 39, wherein the pyrithione salt is sodium pyrithione, zinc pyrithione, copper pyrithione, aluminium pyrithione, or magnesium pyrithione.

41. The method of claim 36, wherein the weight ratio of (a) to (b) is from about 1:30 to about 30:1.

* * * * *